United States Patent [19]

Hunt et al.

[11] Patent Number: 4,479,897

[45] Date of Patent: Oct. 30, 1984

[54] ACTAPLANIN ANTIBIOTICS

[75] Inventors: Ann H. Hunt, Greenwood; Kurt E. Merkel, Mooresville, both of Ind.

[73] Assignee: Eli Lilly and Company, Indianapolis, Ind.

[21] Appl. No.: 488,967

[22] Filed: Apr. 27, 1983

[51] Int. Cl.$^3$ .................... C07C 103/52; C07H 17/08
[52] U.S. Cl. ........................... 260/112.5 R; 536/16.8; 536/18.1
[58] Field of Search ................ 536/18.1, 16.8; 260/112.5 R

[56] References Cited

U.S. PATENT DOCUMENTS

| | | | |
|---|---|---|---|
| 3,928,571 | 12/1975 | Raun | 424/118 |
| 3,952,095 | 4/1976 | Hamill et al. | 424/118 |
| 4,064,233 | 12/1977 | Hamill et al. | 424/118 |
| 4,115,552 | 9/1978 | Hamill et al. | 424/118 |
| 4,322,343 | 3/1982 | Debono et al. | 260/112.5 R |
| 4,322,406 | 3/1982 | Debono et al. | 424/118 |

OTHER PUBLICATIONS

Kalman, et al., *J. Amer. Chem. Soc.*, 102, No. 3 (1980) 897–905.

*Primary Examiner*—Johnnie R. Brown
*Assistant Examiner*—Elli Peseler
*Attorney, Agent, or Firm*—William B. Scanlon; Arthur R. Whale

[57] ABSTRACT

Actaplanin antibiotics (A4696) designated as $C_{2a}$, $D_1$, $D_2$, K, L, M, N, and O are obtained by the partial acidic hydrolysis of known actaplanins at about pH 1.85 for 2.5 hours at about 90° C. The new actaplanins, like the known actaplanins, are glycopeptides which possess antibacterial activity and, either alone or as a mixture with other actaplanins, improve the feed efficiency in ruminants, swine and poultry.

10 Claims, No Drawings

ACTAPLANIN ANTIBIOTICS

BACKGROUND OF THE INVENTION

This invention relates to antibiotics of the glycopeptide class. In particular, it relates to antibiotic substances obtained with the glycopeptide antibiotic actaplanin, also know as A4696.

Antibiotic A4696 is described by Hamill et al., U.S. Pat. No. 3,952,095, and factors A and "B" thereof are described in U.S. Pat. No. 4,115,552. Further, previously unisolated and unrecognized A4696 factors are described by Debono et al., U.S. Pat. No. 4,322,406. Debono, U.S. Pat. No. 4,322,346 also describes the pseudo-aglycone obtained by the complete acid hydrolysis of actaplanin.

The actaplanin antibiotics in addition to their therapeutic usefulness as antibiotics also improve feed efficiency in ruminants, U.S. Pat. No. 3,928,571, as well as swine and poultry, U.S. Pat. No. 4,064,233.

This invention provides hitherto unidentified actaplanin compositions obtained by the partial aqueous acidic hydrolysis of the known actaplanins. The structures of the known actaplanins have been determined and a study of the profile of the hydrolysis products of the known actaplanins under incomplete acid hydrolysis conditions has led to the discovery and structural identification of the new actaplanins described herein.

SUMMARY

The known actaplanin factors are subjected to incomplete acidic aqueous hydrolysis, pH 1.80–1.85 for 2.5 hours at 90° C., to provide mixtures of the starting material and other actaplanins. For example, actaplanin A is hydrolyzed to a mixture of unhydrolyzed A, the known actaplanin $B_3$, and actaplanin $C_{2a}$, $D_1$, $D_2$, and K. The individual actaplanins can be separated from the hydrolysis mixture by $C_{18}$ reverse-phase silica HPLC using aqueous acetonitrile gradients containing triethylamine phosphate.

The actaplanins of this invention like the known actaplanins are useful in enhancing the feed efficiency in ruminants, swine, and poultry when administered in the feed of such animals. They also possess activity against the gram-positive microorganisms.

DETAILED DESCRIPTION

The actaplanin antibiotic compounds of this invention are represented by the following structural formula 1.

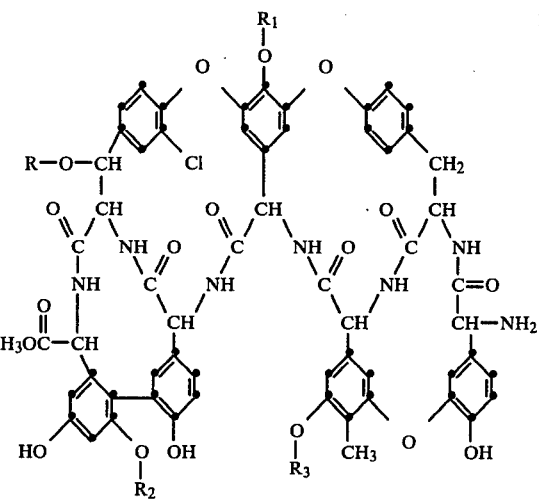

wherein R is L-ristosamine;

$R_1$ is hydrogen, glucosyl, or the disaccharide mannosyl-glucose or rhamnosyl-glucose;

$R_2$ and $R_3$ independently are hydrogen or mannose; with the limitations that when $R_1$ is hydrogen, either or both of $R_2$ and $R_3$ are mannose; when $R_1$ is glucosyl then both $R_2$ and $R_3$ are hydrogen; and when $R_1$ is mannosyl-glucose or rhamnosyl-glucose, $R_2$ is hydrogen; and the pharmaceutically acceptable non-toxic salts thereof.

The actaplanin factors and the pharmaceutically acceptable salts thereof represented by the formula 1, like the known actaplanins, possess antibacterial activity and inhibit the growth of microorganisms pathogenic to man and animals.

The actaplanins of this invention are prepared by acidic hydrolysis of known actaplanins as described hereinafter. Formula 1 represents the eight individual discreet actaplanins comprising the present invention as follows.

| Actaplanin | $R_1$ | $R_2$ | $R_3$ |
|---|---|---|---|
| $C_{2a}$ | H | mannose | mannose |
| $D_1$ | H | mannose | H |
| $D_2$ | H | H | mannose |
| K | mannosyl-glucose | H | mannose |
| L | rhamnosyl-glucose | H | mannose |
| M | mannosyl-glucose | H | H |
| N | rhamnosyl-glucose | H | H |
| O | glucose | H | H |

As shown by the formula 1, the actaplanin antibiotics structurally are comprised of a pseudo-aglycone nucleus (peptide+ristosamine sugar) and neutral sugar moieties attached to the peptide core via phenolic hydroxyl groups. The actaplanin compounds of this invention differ from one another and from the known actaplanins by the nature and/or distribution of the neutral sugars attached to the pseudo-aglycone nucleus. For convenience herein in describing the preparation of the new actaplanins, the following structural formula 2 will be used for reference to the known actaplanins.

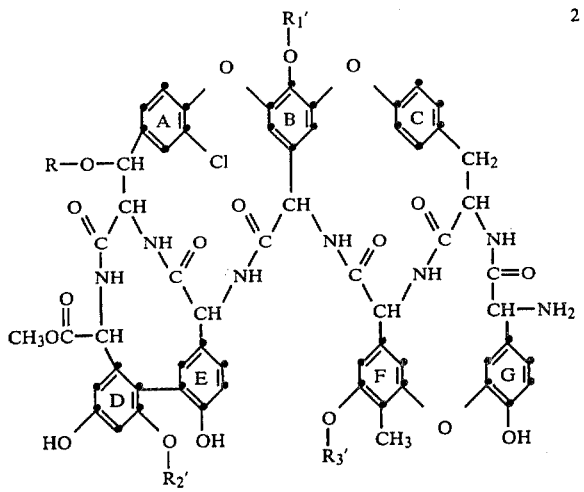

2

The actaplanins identified thus far have either glucose or one of two disaccharides (mannosyl-glucose or rhamnosyl-glucose) attached to the phenolic group of ring B via the 1-position of glucose ($R_1'$), and mannose attached at either ring D ($R_2'$) or ring F ($R_3'$) or at both of these sites.

Complete acidic hydrolysis of the actaplanins provides the pseudo-aglycone nucleus (formula 2, when $R_1'$, $R_2'$, and $R_3'$ are all hydrogen) as described by Debono, U.S. Pat. No. 4,322,343. It has been found that the partial acidic hydrolysis of known actaplanins results in the removal of certain of the sugars at a greater rate than other sugars present to provide the new actaplanins of this invention.

The structure of the known actaplanins which can be used to prepare the actaplanins of this invention are listed in the following TABLE 1.

TABLE 1

| Actaplanin[1] | Structure of Known Actaplanins Formula 2 | | |
|---|---|---|---|
| | $R_1'$ | $R_2'$ | $R_3'$ |
| A | mannosyl-glucose | mannose | mannose |
| $B_1$ | rhamnosyl-glucose | mannose | mannose |
| $B_2$ | glucose | mannose | mannose |
| $B_3$ | mannosyl-glucose | mannose | H |
| $C_{1a}$ | rhamnosyl-glucose | mannose | H |
| G | glucose | mannose | H |
| $C_3$ | glucose | H | mannose |

[1]The indicated actaplanin is described in the following references: A, U.S. Pat. No. 4,115,552; $B_1$, $B_2$, $B_3$ and $C_{1a}$, U.S. Pat. No. 4,322,406; and actaplanin G in copending U.S. appln. S.N. 426,493 filed Sept. 29, 1982.

It will be appreciated from the structures of the known actaplanins that hydrolysis of the sugars of any individual compound at different sites is possible. For example, the disaccharides ($R_1'$) could hydrolyze to monosaccharides and the latter then to the free phenol, $R_1'$ = H. Likewise in compounds wherein $R_2'$ and $R_3'$ are mannose, either or both neutral sugars may be removed and either before or concurrently with the hydrolysis of a disaccharide $R_1'$. However, the nature of the sugar removed as well as its site of attachment and the rate of hydrolysis are factors which render the nature of the partial hydrolysis product or products unpredictable. The study of the partial hydrolysis of the actaplanins under aqueous acidic conditions at elevated temperature has led to a profile of hydrolysis products and the discovery of the actaplanins of this invention.

The partial hydrolysis of the known actaplanin, TABLE 1, was carried out by dissolving the compound in an aqueous solution at pH 1.80–1.85 and heating the solution at 90° C. for 2.5 hours. The hydrolysis mixture was analyzed by HPLC.

Under the above hydrolysis conditions each of the known actaplanins survived hydrolysis in varying degrees and was present in the hydrolysis mixture along with the partial hydrolysis products.

The production of the actaplanins of this invention with the known actaplanins is described in the following paragraphs wherein the percentage yields were obtained by HPLC analysis of the hydrolysis mixture.

Actaplanin $C_{2a}$ (formula 1, $R_1$=H, $R_2$=$R_3$=mannose) is obtained by the hydrolysis of actaplanins A, $B_1$ and $B_2$ in 22%, 16%, and 52% yield, respectively. In all three instances actaplanin $C_{2a}$ was obtained as the major hydrolysis product formed by the removal of the $R_1$ disaccharide or sugar of the known factor.

Actaplanin $D_1$ (formula 1,$R_1$=H, $R_2$=mannose, $R_3$=H) is best obtained by the hydrolysis of actaplanin G. $D_1$ is the major hydrolysis product of G(62%) formed by the removal of the $R_1$ glucose.

Actaplanin $D_2$ (formula 1, $R_1$=H, $R_2$=H, $R_3$=mannose) is isomeric with factor $D_1$ and is produced by the hydrolysis of actaplanin $C_3$ by removal of the $R_1$ glucose from $C_3$.

Actaplanin K (formula 1, $R_1$=mannosyl-glucose, $R_2$=H, $R_3$=mannose) is obtained as a minor product of the hydrolysis of actaplanin A. The major product, as noted above, is factor $C_{2a}$. Actaplanin K occurs as about 4% of the hydrolysis products obtained by acid hydrolysis of the $R_2$ mannose of A without removal of the disaccharide.

Actaplanin L (formula 1, $R_1$=rhamnosyl-glucose, $R_2$=H, $R_3$=mannose) is obtained as about 2% of the hydrolysis products of actaplanin $B_1$ by removal of the $R_2$ mannose of $B_1$. As with actaplanin A, the major product of the hydrolysis of $B_1$ is actaplanin $C_{2a}$ occurring by removal of the disaccharide $R_1$. In A the disaccharide is mannosyl-glucose while in $B_1$ the $R_1$ disaccharide is rhamnosyl-glucose.

Actaplanin M (formula 1, $R_1$=mannosyl-glucose, $R_2$=$R_3$=H) is obtained as about 4% of the hydrolysis of actaplanin $B_3$ (formula 2, $R_1$=mannosyl-glucose, $R_2$=mannose, $R_3$=H) occurring by removal of the $R_2$ mannose of $B_3$. It should be noted that the hydrolysis of A under the conditions described hereinabove also produces actaplanin $B_3$ as a minor hydrolysis product via removal of the $R_3$ mannose. Since $B_3$ is present in the hydrolysis of A, it can also be converted in the hydrolysis to actaplanin M (removal of remaining mannose, $R_2$). However, the major hydrolysis product of $B_3$ is actaplanin $D_1$.

Actaplanin N (formula 1, $R_1$=rhamnosyl-glucose, $R_2$=H, $R_3$=H) is obtained as about 3% of the hydrolysis products of actaplanin $C_{1a}$ (formula 2, $R_1$=rhamnosyl-glucose, $R_2$=mannose, $R_3$=H) by removal of the $R_2$ mannose of $C_{1a}$. As with the hydrolysis of $B_3$, the major product obtained by the hydrolysis of $C_{1a}$ is actaplanin $D_1$ which occurs via removal of the disaccharide $R_1$.

Actaplanin O (formula 1, $R_1$=glucose, $R_2$=$R_3$=H) is best obtained by the hydrolysis of actaplanin G. Alternatively it is obtained as a minor product of the hydrolysis of actaplanin $C_{1a}$ along with actaplanin N as described above. Actaplanin O occurs as about 1% of the hydrolysis products via hydrolytic splitting of the rhamnosyl portion of the $R_1$ rhamnosyl-glucose disaccharide and the removal of the $R_2$ mannose.

Actaplanin O also is produced in minor amounts in the hydrolysis of actaplanin $B_2$ ($R_1$=glucose, $R_2$=$R_3$=mannose) via removal of both mannose sugars, $R_2$ and $R_3$.

The actaplanin compounds of this invention can be isolated from the hydrolysis mixture and separated from other hydrolysis products and the starting material by chromatography. They may be separated by column chromatography, preparative thin layer chromatography, or by preparative high performance liquid chromatography (HPLC).

The profile of components obtained in the incomplete acidic hydrolysis of the known actaplanins is shown in TABLE 2.

TABLE 2

Composition of Actaplanin Incomplete Hydrolysis Mixtures

| Component | Percent Component[1] Known Actaplanin | | | | | |
|---|---|---|---|---|---|---|
|  | A | $B_1$ | $B_2$ | $B_3$ | $C_{1a}$ | G |
| A | 56% | — | — | — | — | — |
| $B_1$ | — | 63 | — | — | — | — |
| $B_2$ | trace | 7 | 19 | — | — | — |
| $B_3$ | 6 | — | — | 55 | — | — |
| $C_{1a}$ | — | 3 | — | — | 32 | — |
| G | — | — | 3 | 2 | 9 | 21 |
| K | ca.4 | — | — | — | — | — |
| L | — | — | — | — | — | — |
| M | — | — | — | 4 | — | — |
| N | — | — | — | — | 3 | — |
| O | — | — | ca.5 | — | 1 | 2 |
| $C_{2a}$ | 22 | 16 | 52 | — | — | — |
| $D_1$ | | | | 31 | 46 | 62 |
| $D_2$ | 4[2] | 2 | 17 | — | — | — |
| aglycone | | | 2 | 5 | 6 | 9 |

[1]The "—" indicates that the particular component is not a possible hydrolysis product. A blank indicates that the component was not observed in the hydrolysis mixture.
[2]The percentages are for $D_1$ and $D_2$ combined.

The structures of the actaplanins were determined by a study of the nuclear magnetic resonance spectra of the various factors including decoupling studies and NOE observations, the identity of the sugars obtained by hydrolysis, and by HPLC analysis (retention times).

The actaplanins of this invention are structurally represented by the above formula 1. As is shown, the sugars attached to the pseudo-aglycone phenolic nucleus are attached to the phenolic hydroxyl of rings B, D, and F (formula 2). When $R_1$ is a mannosyl-glucose or rhamnosyl-glucose disaccharide (actaplanins K, L, M, and N), the glucose moiety is attached to the phenolic group at the 1-position while the mannose or rhamnose is in turn attached to the glucose moiety. Likewise, when $R_1$ is glucose the glucose is attached at the 1-position (actaplanin O). The mannose sugars are also attached at the phenolic sites $R_2$ and $R_3$ at the 1-position.

The actaplanin compounds of this invention, like the known actaplanins, are soluble in water and polar organic solvents. The actaplanins form salts with suitable acids such as hydrochloric, sulfuric, phosphoric, and nitric acids. Such salts are pharmaceutically acceptable forms of the antibiotics and may be used in formulations for administration. These salts are prepared by conventional salt-forming methods, eg., an aqueous solution of the compound is treated with the acid and the salt formed is precipitated by the addition of an antisolvent to the salt solution.

In using the actaplanins of this invention to improve the feed efficiency of ruminants, the individual factors or any combination thereof as a mixture may be incorporated in the feed or drinking water of the ruminant as either the free base form or preferably as the salt form, eg., the hydrochloride salt. Likewise, the individual antibiotics or any combination thereof may be administered to the infected host to control infections caused by gram-positive microorganisms, eg., staphylococcus and streptococcus.

EXAMPLE 1

Hydrolysis Procedure for Actaplanins

An aqueous solution of the actaplanin at a concentration of 0.5 mg./ml. was acidified with aqueous 2.5 N hydrochloric acid to pH 1.80–1.85. The solution was then heated on the steam bath (solution temperature=90° C.). After heating for 2.5 hours an aliquot of the solution was withdrawn for HPLC analysis.

The analysis and detection of the components of the hydrolysis mixture was carried out with a liquid chromatograph (Water Associates, Milford, Massachusetts) equipped with a Model 660 solvent programmer, two Model 6000 solvent delivery systems, a Model 440 absorbance detector, a Model U6K injector and a μ-Bondapak $C_{18}$ column (300×3.9 mm.). HPLC mobile phase: Solvent A=2% aqueous acetic acid/acetonitrile (90/10, v/v) and solvent B=2% aqueous acetic acid/acetonitrile (70/30, v/v). Flow rate: 0.8 ml./min. Pressure: 850 psi. Detector: 0.02 Aufs. (UV, 254 nm). Solvent Programmer Settings: 0–100% solvent B, curve 7, 30 minutes.

The following TABLE 3 lists the retention factors, K', for the actaplanin compounds of this invention.

TABLE 3

| Actaplanin HPLC Retention Factors | |
|---|---|
| Actaplanin | K'-Value |
| $C_{2a}$ | 7.12 |
| $D_1 + D_2$ | 7.37 |
| K | 1.93 |
| L | 2.38 |
| M | 3.59 |
| N | 3.98 |
| O | 4.98 |

The K' values in the above TABLE 3 were adjusted for meaningful comparison with those of the known actaplanins A, $B_1$, $B_2$, $B_3$, $C_{1a}$, $C_3$, and $E_1$ as assigned in U.S. Pat. No. 4,322,406 and for actaplanin G in copending application Ser. No. 426,493. The adjustment was made for comparison with the published K' values since the HPLC system used for the published K' values differed slightly from the HPLC system used herein. The assignment and comparison of K' values is most consistent if observed values are determined under identical HPLC conditions or by comparison with compounds of very similar retention times. The incomplete hydrolysis of the pure actaplanins under the conditions described above resulted in mixtures of the starting material and hydrolysis products. The retention times of the products, K, L, M, N, and O, are only slightly longer than those of the parent actaplanins. The HPLC peaks corresponding to the starting material therefore can be used as markers for the determination of the K' differences between the known actaplanin and the new actaplanins in the hydrolysis sample. These differences, ΔK' values, were in each case obtained from the separation between the peak of the starting material and the new actaplanin. The ΔK' value was then added to the previously assigned and published K' value of the known actaplanin as shown below.

| Actaplanin | K' | ΔK' | Actaplanin | K' |
|---|---|---|---|---|
| A | 1.60 | 0.33 | K | 1.93 |
| $B_1$ | 1.99 | 0.39 | L | 2.38 |
| $B_3$ | 2.50 | 1.09 | M | 3.59 |
| $C_{1a}$ | 2.92 | 1.06 | N | 3.98 |
| G | 4.42 | 0.56 | O | 4.98 |

We claim:

1. A compound of the formula

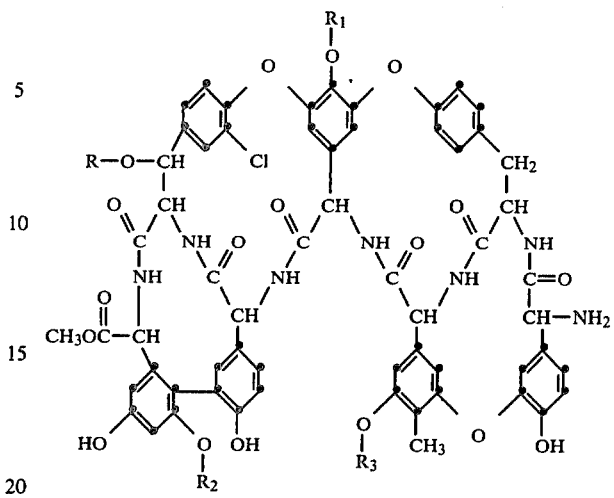

wherein R is L-ristosamine;
$R_1$ is hydrogen, glucosyl, or the disaccharide mannosyl-glucose or rhamnosyl-glucose;
$R_2$ and $R_3$ independently are hydrogen or mannose; with the limitations that when $R_1$ is hydrogen, either or both of $R_2$ and $R_3$ is or are mannose; when $R_1$ is glucosyl, $R_2$ and $R_3$ are both hydrogen; and when $R_1$ is a disaccharide, $R_2$ is hydrogen; and the pharmaceutically acceptable non-toxic salts thereof.

2. The compound of claim 1 wherein $R_1$ is hydrogen and $R_2$ and $R_3$ are mannose.

3. The compound of claim 1 wherein $R_1$ is hydrogen and either of $R_2$ and $R_3$ is mannose.

4. The compound of claim 1 wherein $R_1$ is mannosyl-glucose.

5. The compound of claim 4 wherein $R_2$ is hydrogen and $R_3$ is mannose.

6. The compound of claim 4 wherein $R_2$ and $R_3$ are both hydrogen.

7. The compound of claim 1 wherein $R_1$ is rhamnosyl-glucose.

8. The compound of claim 7 wherein $R_2$ is hydrogen and $R_3$ is mannose.

9. The compound of claim 7 wherein $R_2$ and $R_3$ are both hydrogen.

10. The compound of claim 1 wherein $R_1$ is glucose.

* * * * *